(12) United States Patent
Lai

(10) Patent No.: US 6,757,310 B2
(45) Date of Patent: Jun. 29, 2004

(54) SOLID-STATE LASER FOR CUSTOMIZED CORNEA ABLATION

(76) Inventor: Ming Lai, P.O. Box 10845, Pleasanton, CA (US) 94588

( * ) Notice: Subject to any disclaimer, the term of this patent is extended or adjusted under 35 U.S.C. 154(b) by 208 days.

(21) Appl. No.: 10/051,975

(22) Filed: Jan. 16, 2002

(65) Prior Publication Data

US 2002/0095142 A1 Jul. 18, 2002

Related U.S. Application Data

(60) Provisional application No. 60/262,163, filed on Jan. 17, 2001.

(51) Int. Cl.$^7$ ................................................ H01S 3/14
(52) U.S. Cl. ............................... 372/39; 372/5; 372/41; 372/75
(58) Field of Search ............................... 372/5, 41, 28, 372/92

(56) References Cited

U.S. PATENT DOCUMENTS

| 5,144,630 A | 9/1992 | Lin |
| 5,520,679 A | 5/1996 | Lin |
| 5,546,222 A | 8/1996 | Plaessmann et al. |
| 5,615,043 A | 3/1997 | Plaessmann et al. |
| 5,632,742 A | 5/1997 | Frey et al. |
| 5,777,719 A | 7/1998 | Williams et al. |
| 5,949,521 A | 9/1999 | Williams et al. |
| 6,031,854 A | 2/2000 | Ming |
| 6,179,422 B1 | 1/2001 | Lai |
| 2002/0096242 A1 * | 7/2002 | Wasitis et al. ............... 156/71 |

OTHER PUBLICATIONS

Hirlimann et al., Femtosecond Jet Laser Preamplifier, Optics Communications, vol. 59, No. 1, pp 52, Aug. 1, 1986.
Chen et al., Recent Developments in Barium Borate, SPIE Proceedings, vol. 681, No. 12, pp 12–19, 1986.
Umemura et al., New data on the phase–matching properties of $CsLiB_6O_{10}$, OSA TOPS vol. 26, Advanced Solid–State Lasers, 1999, p. 715.
Backus et al., 0.2–TW laser system at 1 kHz, Optics Letters, vol. 22, No. 16, Aug. 15, 1997.

* cited by examiner

*Primary Examiner*—Leon Scott, Jr.

(57) ABSTRACT

A diode pump, solid state laser deep UV laser source is described for customized ablation in photo-refractive surgery. The solid-state deep UV laser source is tailored to have a pulse repetition rate of about 1 kHz and a relatively small spot size at both positions of the cornea and the scanner. Such a deep UV laser source enables the use of fast scanner and the implement of fast eye tracker. One embodiment of such a deep UV laser source comprises a passively Q-switched microchip laser, a diode-pumped multiple pass amplifier, and a wavelength converter.

20 Claims, 3 Drawing Sheets

SOLID-STATE LASER FOR CUSTOMIZED CORNEA ABLATION

This application claims the benefit of U.S. Provisional Application Ser. No. 60/262,163, filed on Jan. 17, 2001.

FIELD OF THE INVENTION

The present invention relates to method and apparatus for generating a solid-state deep UV laser source. In particular, the present invention relates to generate a solid-state deep UV laser source for customized cornea ablation in photo-refractive surgery.

BACKGROUND OF THE INVENTION

Topography link and/or wavefront guided custom ablation can potentially improve the outcome of photo-refractive surgery to achieve supernormal visual acuity. In a custom-ablation photo-refractive surgery, a computer of the surgical system reads in the patient's data from a topography or wavefront device and controls the scan of a surgical laser beam to generate a customized ablation profile. It can thus remove corneal irregularity and correct low and high order of refractive errors. In comparison, conventional photo-refractive surgery removes only low order of refractive errors, such as defocusing and astigmatism. In many circumstances, conventional photo-refractive surgery induces extra amount of high order refractive errors and leads to imperfections such as halo and night vision.

The advantageous custom-ablation procedure requires a fine and precise control of laser energy deposition on the cornea with a fast and accurate compensation of the eye movement. Therefore, it is greatly desirable to have a small ablation beam with stable pulse energy, a scanner with high scanning speed, and an eye-tracking device with fast response.

Currently, focused excimer laser beam scanned by a computer-controlled scanner is the only modality to perform custom-ablation surgery. Due to some intrinsic limitations, however, excimer lasers are far from an ideal laser source for this delicate application.

One limitation of excimer lasers is a large pulse-to-pulse energy fluctuation. A fluctuation of 20% or more is common for excimer refractive lasers. This fluctuation degrades significantly the achievable accuracy of energy deposition on the cornea.

Another limitation of excimer lasers is a low repetition rate of pulse generation. A pulse repetition rate of 100 Hz or lower is typically used for refractive surgery. Higher repetition rate usually leads to bigger pulse-to-pulse fluctuation and degrades laser performance. Because ablation time of the custom ablation surgery is preferable to be similar to that of conventional surgery, this low repetition rate limits the beam spot size to about 1-mm on the cornea and thus limits the fineness of ablation profile.

A further limitation of excimer lasers is its poor beam quality. A typical excimer has a rectangular beam profile, and the intensity distribution varies across the beam and changes with the age of laser optics and discharge electrodes. Usually, the beam collimation is poor and the beam spot size on the scanner is big. The scanner mirror, thus, has to be big. Speed of the scanner is limited by the rotation inertia of the mirror and, consequently, poor beam quality of excimer lasers means a slow scanner. A slow scanner prohibits precise disposition of pulses at high repetition rate and forbids fast response of eye tracking.

SUMMARY OF THE INVENTION

The present invention recognizes the special needs for custom ablation in photo-refractive surgery and contemplates a solid-state deep UV laser to overcome the above-identified limitations of excimer lasers. In a preferred embodiment described in this disclosure, a solid state laser is designed to meet the special needs for custom-ablation in photo-refractive surgery.

Accordingly, an objective of the present invention is to provide a new and improved deep UV laser source for customized ablation in photo-refractive surgery.

Another objective of the present invention is to provide a new and improved laser source to enable the implement of fast scanning and fast eye tracking for customized ablation in photo-refractive surgery.

A further objective of the present invention is to provide a new and improved laser source to enable fine and precise control of laser ablation profile for customized ablation in photo-refractive surgery.

Another further objective of the present invention is to provide a new and improved solid-state deep UV laser source with kilohertz pulse rate and nanosecond pulse duration.

In an embodiment of a solid-state deep UV laser source designed for custom ablation in photo-refractive surgery, an apparatus of the present invention comprise:

A diode pumped laser oscillator producing nanosecond pulses at a kilohertz pulsed rate, wherein said oscillator is operated at a wavelength around 800 or 1000 nm and generates a pulsed laser beam close to diffraction limit;

A multiple pass, diode pumped laser amplifier amplifying the nanosecond laser pulses to a mJ level;

A wavelength converter converting the amplified pulses to a wavelength around 200 nm and generating deep UV laser pulses to 100-microWatt level.

In a preferred embodiment, the oscillator is a passively-Q-switched microchip laser manufactured by Nanolase of Meylan, France. The microchip laser is modified to pump with a diode laser at a predetermined pulse rate of about 1000 Hz. This microchip laser can produce sub-nanosecond pulses with pulse energy up to 6 $\mu$J at 1064 nm.

In the preferred embodiment, the multiple passes, diode pumped laser amplifier adapts a configuration tough by Hirlimann et al. in Femtosecond Jet Laser Preamplifier, Optics Communications, Vol. 59, No. 1, PP 52, Aug. 1, 1986. The modified configuration enables smaller angular spread of the multiple passes and thus better energy extraction efficiency from the amplifier.

In this preferred embodiment, the wavelength converter adapts an arrangement depicted by Chen et al. in Recent Developments in Barium Borate, SPIE Proceedings, Vol. 681, No. 12, PP 12–19, 1986. The modified wavelength converter employs different non-linear crystals in different stages of harmonics generation to optimize the beam quality and conversion efficiency.

In this preferred embodiment, the solid-state deep UV laser source is tailored to operate at about 1000 Hz and to have pulse energy of about 0.2 mj at a wavelength of 210 nm. The pulse duration is about 1 nanosecond. This pulse duration is particularly chosen to be short enough to generate deep UV efficiently and to be long enough to avoid expensive mode-locking technology. The spot size of the laser beam is about 0.3 mm on cornea and about 1 mm on the scanner mirror. The pulse to pulse fluctuation of this laser source is smaller than 10%, and the quality of the deep UV beam is near diffraction limit.

Consequently, the tailored solid-state deep UV laser source enables the generation of fine-ablation profile for refractive surgery. With a near diffraction-limited beam quality, this laser source makes it possible to use small scanner mirror for achieving fast scanning and engaging fast eye tracking.

The above and other objectives and advantages of the present invention will become more apparent in the following drawings, detailed description, and claims.

DETAILED DESCRIPTION OF THE DRAWINGS

Figure 1:
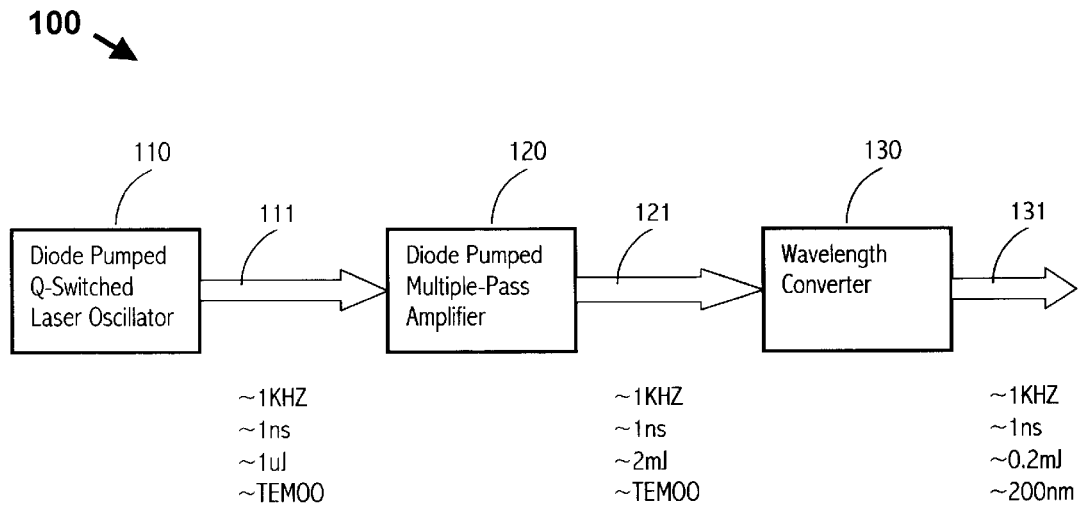
FIG. 1 is a block diagram of a solid-state deep UV laser source tailored for customized cornea ablation in accordance with the present invention.

FIG. 1 is a block diagram of a solid-state deep UV laser source 100 tailored for customized cornea ablation in accordance with the present invention. The deep UV laser source 100 consists of a diode-pumped Q-switched laser oscillator 110, a diode pumped multiple-pass amplifier 120, and a wavelength converter 130. This laser source 100 produces deep UV laser pulses with a wavelength around 200 nm, a pulse rate around 1 kHz, and pulse energy around 0.2 mJ.

The laser oscillator 110 produces specifically laser pulses with a pulse rate around 1 kHz, pulse duration around 1 ns, and a wavelength around 800 or 1000 nm. The pulsed laser beam 111 is substantially at TEM00 mode. The pulse rate around 1 kHz is preferred for optimal customized ablation in photo-refractive surgery. The pulse duration around 1 ns and near TEM00 mode are required to achieve effective deep UV conversion without optical damage in non-linear crystal. The wavelength around 800 or 1000 nm is required to produce deep UV around 200 nm through $4^{th}$ or $5^{th}$ harmonic generation. Ti:sapphire and Cr:LiSAF are examples of laser crystals for obtaining wavelength around 800 nm. Nd:YAG, Nd:YLF, Nd:YVO, and Yb:YAG are examples of laser crystals for obtaining wavelength around 1000 nm.

Figure 2:
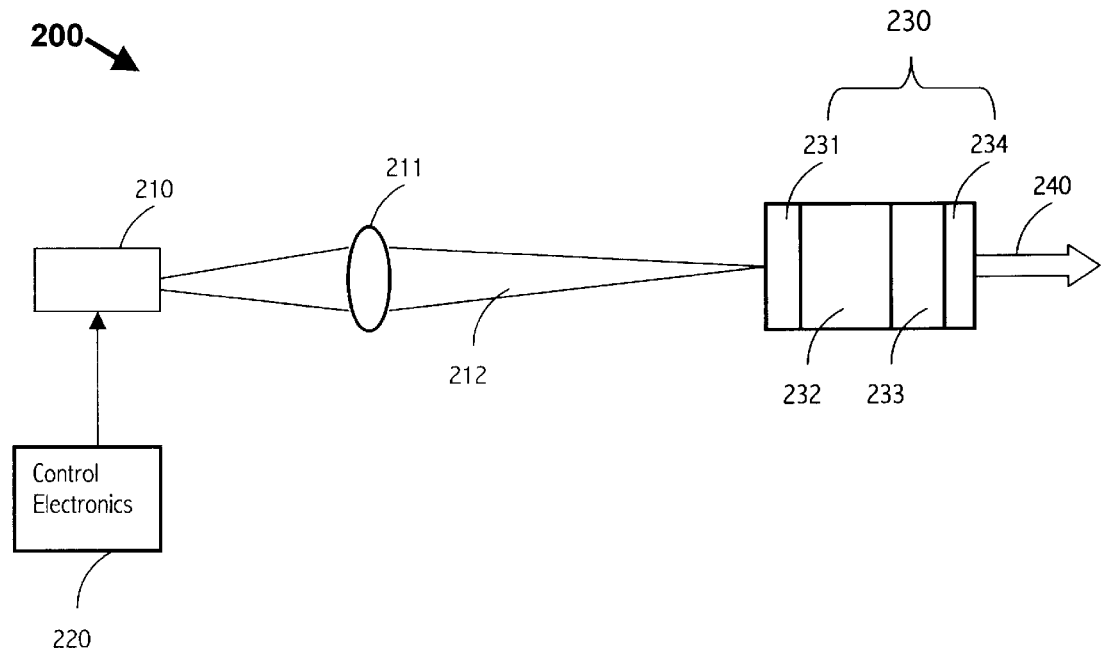
FIG. 2 shows a prior-art microchip laser module that is passively Q-switched to produce nanosecond pulses at a controllable kilohertz pulse rate.

The laser oscillator 110 is diode pumped to achieve both short term and long term stability of laser pulse energy. This pulse energy stability is essential for optimal custom ablation in photo-refractive surgery. The laser oscillator 110 is Q-switched to avoid the expensive mode-locking technology. In particular, Q-switched microchip laser can be much reliable and compact. As shown in FIG. 2, a diode-pumped, passively Q-switched microchip laser is desirable for this application.

The multiple-pass amplifier 120 amplifies specifically laser pulses to m-Joule level at kilohertz pulse rate and nanosecond pulse duration. The amplified laser beam 121 maintains substantially TEM00 mode quality.

Pulse energy on the m-Joule level is required to generate enough pulse energy at deep UV for photo-refractive surgery. The amplifier 120 uses a multiple pass configuration to achieve combined advantages of simplicity, compact, and efficiency for this energy level. The amplifier 120 is diode pumped to obtain reliability and safety for medical applications. In a preferred embodiment depicted in FIG. 4, a multiple pass amplifier with smaller angular spread is desirable for extracting more efficiently energy from the amplifier.

The wavelength converter 130 converts the amplified beam 121 to a deep UV laser beam 131 at a wavelength around 200 nm. The wavelength converter 130 uses non-linear optical crystals including PTK, LBO, BBO, and CLBO. Two or three pieces of non-linear crystals can be used to converter a wavelength around 800 nm to a deep UV wavelength around 200 nm through harmonic or sum frequency process. Three pieces of non-linear crystals are used to converter a wavelength around 1000 nm to a deep UV wavelength around 200 nm through harmonic and sum frequency processes. The non-linear crystals and wavelength conversion processes are well known in the prior art. In a preferred embodiment depicted in FIG. 6, three pieces of different non-linear crystals are used to optimize the conversion efficiency of deep UV generation.

FIG. 2 shows a prior-art microchip laser module 200 that is passively Q-switched to produce a pulsed laser beam 240 at a controllable kilohertz pulse rate and sub-nanosecond pulse duration. The microchip laser 200 comprises a microchip laser 230 pumped by a diode laser 210, which is in turn controlled by a control electronics 220.

The microchip laser 230 consists of a gain medium 232 and a saturable absorber enclosed by an input mirror 231 and an output mirror 234. The gain medium 232 is a solid-state laser crystal Nd:YAG and the saturable absorber 233 is another solid-state crystal Cr:YAG. The input mirror 231 and the output mirror 234 form a resonant cavity for the laser wavelength at 1064 nm.

A pumped laser beam 212 from the diode laser 210 is focused with a lens 211 onto the gain medium 232, through the input mirror 231. The pumped laser beam 212 is at a wavelength of 808 nm. The input mirror 231 has a dielectric coating allowing high reflection at the laser wavelength 1064 and high transmission at the pumped laser wavelength 808 nm. The output mirror 234 has a dielectric coating of partial transmission at the laser wavelength of 1064 nm.

The saturable absorber 233 is a passive Q-switching element. It absorbs energy at an initial time and the laser cavity has high loss and thus low Q-value. The absorber 233 saturates at a threshold and suddenly becomes transparent within a sub-nanosecond time scale. This way the laser cavity switches to a high Q-value and a short laser pulse is generated.

When pumped with continuous-wave beam, the passively Q-switched microchip laser produces sub-nanosecond laser pulses at a repetition rate of hundred kilohertz and pulse energy of several micro-Joules. Such a microchip laser 200 is commercially available from Nanolase of Meylan, France.

To achieve a preferable pulse rate around 1 kHz, control electronics 220 is used to control the repetition rate and the pulse duration of the pumped laser beam 212. This way, the diode-pumped, passively Q-switched microchip laser 200 can produces sub-nanosecond pulses at a controllable repetition rate around 1 kHz, a wavelength at 1064 nm, and a pulse energy of several micro-Joules.

Figure 3:
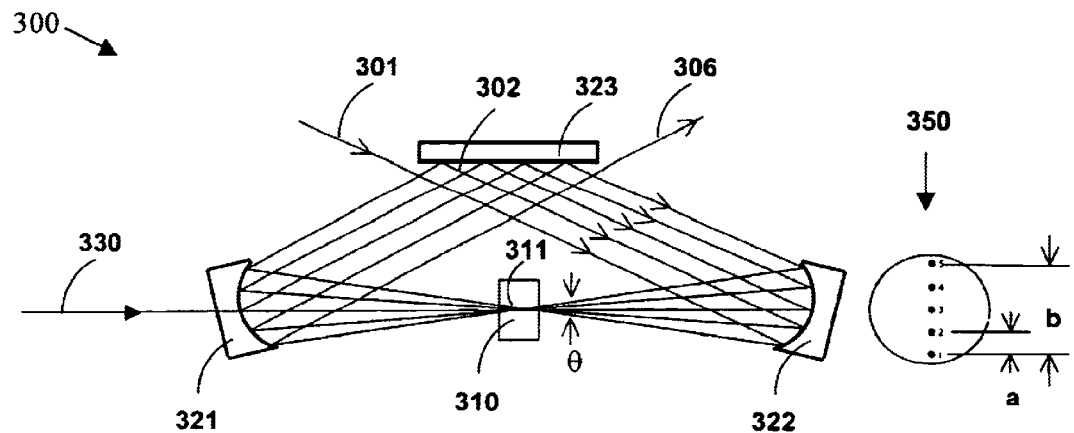
FIG. 3 illustrates a prior-art multiple-pass amplifier that enables multiple passes in a simple configuration.

FIG. 3 illustrates a prior-art multiple-pass amplifier 300 that enables multiple passes in a simple configuration. The amplifier 300 comprises a gain medium 310, two identical concave mirrors 321 and 322, and a flat mirror 323. A pump laser beam 330 is focused onto the gain medium 310 to provide gain for the amplifier 300. The configuration and alignment of amplifier 300 is detailed by Hirlimann et al. in Femtosecond Jet Laser Preamplifier, Optics Communications, Vol. 59, No. 1, PP 52, Aug. 1, 1986.

As shown in FIG. 3, the two concave mirrors 321 and 322 are arranged in a near con-focal configuration and the gain medium 310 is located at the con-focal center 311. The two mirrors 321 and 322 are tilted slightly, such that a collimated input beam 301 to be amplified can be directed onto a concave mirror 322 and focused into the gain medium 310. This input beam 301 is re-collimated by concave mirror 321 and reflected by flat mirror 323 back onto concave mirror 322. The flat mirror 323 is aligned normal to the symmetric axis of the configuration. This way the reflected beam 302 is parallel to the input beam 301 and refocused to the con-focal center 311.

The input beam 301 is thus trapped in the three-mirror configuration for multiple passes until exits as output beam 306.

All beam paths in FIG. 3 lay on a symmetric plane of the three-mirror configuration. For a given focal length of the concave mirrors 321 and 322, the separation between two reentered beams, e.g., 301 and 302, depends on the tilt angle of the two concave mirrors 321 and 322 and the distance from the flat mirror 323 to the con-focal center 311. Increasing the tilt angle and reducing the distance will decrease the separation between the reentered beams.

Insert 350 is a side view of the concave mirror 322 to show the sequential reflection spots of the input beam 301 on mirror 322. The number 1–5 refer to the first to the fifth pass of the amplified beam on the mirror 322. Obviously, the separation a between two neighboring spots is limited by the beam size on the mirror 322 and the spread angle θ of all the beam paths is proportional to the total beam spread b on the mirror 322. This spread angel θ thus depends on the beam spot size on the mirror 322 and the number of passes in the amplifier. To obtain optimum energy extraction from the amplifier 300, it is desirable to have a minimal spread angle θ.

Figure 4:
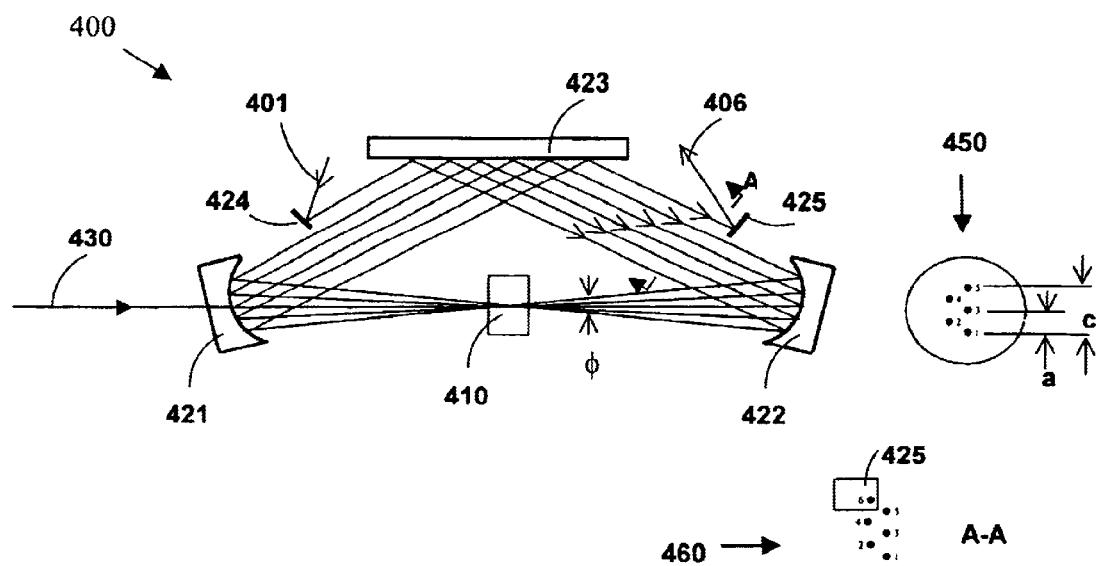
FIG. 4 depicts a modified multiple-pass amplifier that enables multiple passes with a smaller angular spread.

FIG. 4 depicts a modified multiple-pass amplifier 400 that enables multiple passes with a smaller angular spread θ. An input mirror 424 and an output mirror 425 are added into the configuration of the previous amplifier 300. An input beam 401 to be amplified is directed into the amplifier 400 via the input mirror 424, and the amplified beam 406 is directed out the amplifier 400 via the output mirror 425.

Insert 450 is a side view of the concave mirror 422 to show the sequential reflection spots of the input beam 401 on mirror 422. Similar to the spot pattern on concave mirror 322, the number 1–5 here refer to the first to the fifth pass of the amplified beam on the concave mirror 422. Different from the spot pattern on concave mirror 322, the spots on concave mirror 422 dispose on two vertical lines. Obviously, the separation a between two neighboring spots is still limited by the beam size on the mirror 422. The spread angle φ of all the beam paths is now, however, proportional to the beam-spread c on the mirror 422. This spread angel φ can thus be made smaller than the spread angle θ of Figure 300, for the same number of passes.

Insert 460 is a cross section view along plane AA to show how the output mirror 425 is positioned in respect to the other beam paths. The spot labeled #6 refers to the output beam position on mirror 425. The output beam 406 is steered out from the amplifier 400 via this mirror 425. A similar layout is arranged for the input mirror 424 to introduce the input beam 401 into the amplifier 400.

In amplifier 400, the gain medium 410 is a solid state crystal including Ti:sapphire, Cr:LiSAF, Nd:YAG, Nd:YLF, Nd:YVO, and Yb:YAG. The gain medium 410 to be used depends on the wavelength of the input beam 401 to be amplified. Ti:sapphire and Cr:LiSAF are used for wavelength around 800 nm. Nd:YAG, Nd:YLF, Nd:YVO, and Yb:YAG are used for wavelength around 1000 nm. A diode laser pump beam 430 is focused onto the gain medium 410 to provide gain for the amplifier 400. The wavelength of the pump laser 430 depends on the gain medium 410 selected.

In a preferred embodiment, the input beam 401 to be amplified is delivered from a passively Q-switched microchip laser 200 of FIG. 2. The input beam 401 is thus of nanosecond pulses at a wavelength of 1064 nm, a pulse rate around a kilohertz, and pulse energy of several micro-Joule. The gain medium 410 is preferably Nd:YLF pumped by a diode laser beam 430 at a wavelength of 798 nm. The pump diode-laser beam 430 is delivered from a fiber coupled diode laser. The diode laser is operated at continuous wave mode and produces a power of 20 W. Such a diode laser is commercial available form, for example, OPTO Power Corporation of Tucson, Ariz. The amplified beam 406 has pulse energy of approximate 2 mJ.

Alternatively, the gain medium 410 can be Yb:YAG pumped by a diode laser beam 430 at a wavelength of 940 nm. This gain medium Yb:YAG is less mature in comparison with Nd:YLF technology. However, many parameters of this gain medium are more suitable for the amplifier 400. In particular, Yb:YAG lases at 1032 nm while pumped at 940 nm. The quantum efficiency is much higher than Nd:YLF. Also, the up-state lifetime of Yb:YAG is about twice as long as that of Nd:YLF. This longer up-state lifetime makes Yb:YAG more suitable to operate at repetition rate around 500–1000 Hz.

Another alternative of gain medium 410 is Cr:LiSAF operating at a wavelength around 840 nm. The advantage of this gain medium is that it can be pumped by diode laser at wavelength around 670 nm.

Figure 5:
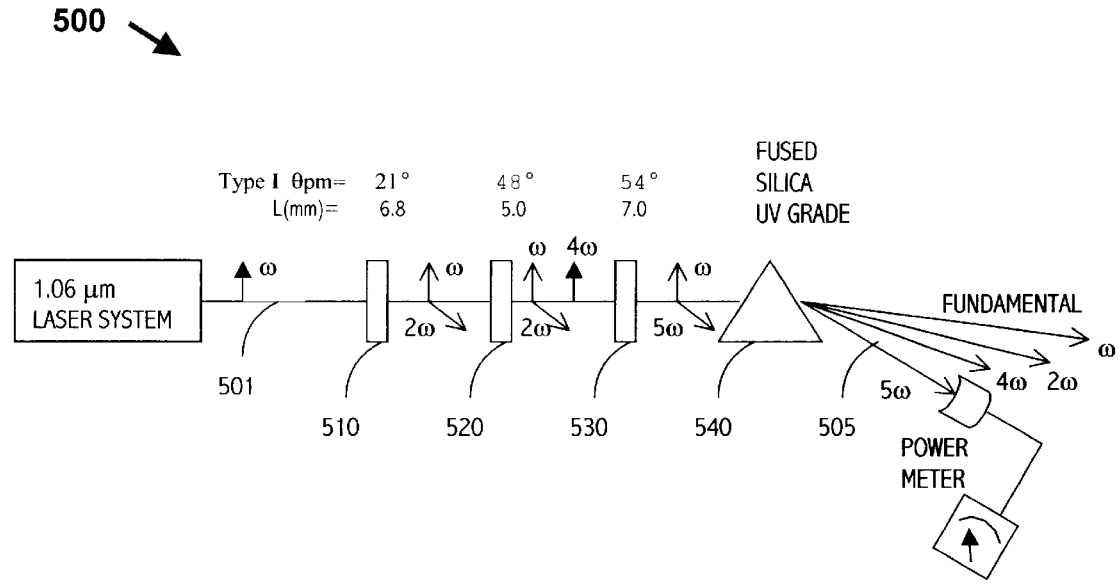
FIG. 5 is a prior-art wavelength converter that produces a deep UV laser beam through a fifth harmonics generation.

FIG. 5 is a prior-art wavelength converter 500 that produces a deep UV laser beam 505 through fifth harmonics generation. The converter 500 consists of three BBO crystals 510, 520 and 530 for second, fourth, and fifth harmonic generation respectively. An UV grade fused silica prism 540 is used to separate the beams at different wavelengths. The crystal fabrication and alignment of the converter 500 is detailed by Chen et al. in Recent Developments in Barium Borate, SPIE Proceedings, Vol. 681, No. 12, PP 12–19, 1986.

BBO is a popular nonlinear crystal having the highest nonlinear coefficient among the other nonlinear crystals including KTP, LBO, and CLBO. BBO has, on the other hand, large walk-off angle and narrow spectral acceptance bandwidth leads to a degraded beam quality and limits overall conversion efficiency for multiple stage, high order harmonic generation. Experiment has shown that LBO is a better choice for the first stage of a multiple-stage converter. In term of overall conversion efficiency, CLBO is a better choice for the second and third stages for a three-stage converter like the wavelength converter 500. CLBO is a relatively new and delicate crystal in comparison to BBO and LBO. As the fabrication and handling technology becomes mature, CLBO will be a crystal of choice for deep UV generation.

Figure 6:
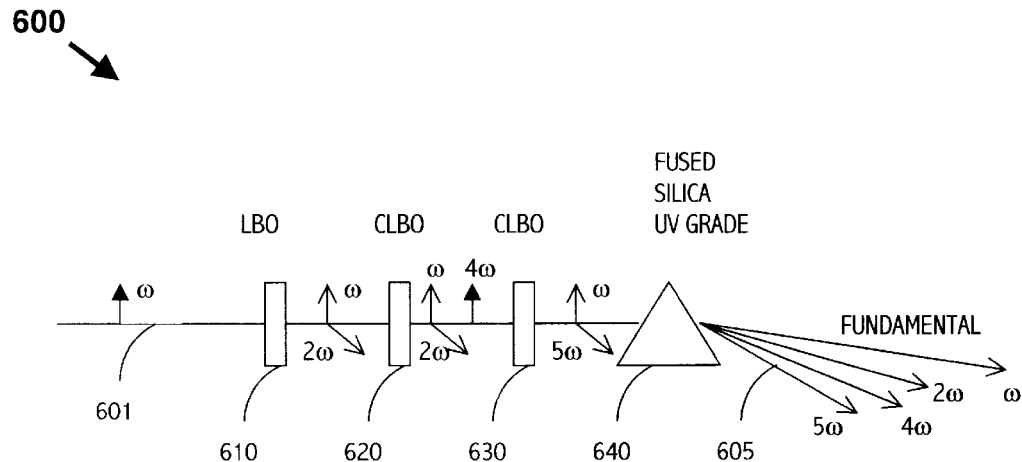
FIG. 6 depicts a modified wavelength converter that enables better beam quality and conversion efficiency for deep UV generation.

FIG. 6 depicts a modified wavelength converter 600 that enables better beam quality and conversion efficiency for deep UV generation. The converter 600 consists of three non-linear crystals 610, 620 and 630 for second, fourth, and fifth harmonic generation respectively. An UV grade fused silica prism 640 is used to separate the beams at different wavelengths.

In this modified wavelength converter 600, the first crystal 610 is a LBO. The crystal 610 is cut type I phase matching to converter an input pulse laser beam 601 at a wavelength 1064 nm to a wavelength 532 nm. The second crystal 620 is a CLBO, which is cut type I phase matching to converter the second harmonic at 532 nm to the fourth harmonic at 266 nm. The third crystal 630 is also a CLBO, which is cut type I phase matching to generate sum frequency at 213 nm.

In a preferred embodiment, the input beam 601 is delivered from a diode pumped multiple pass amplifier 400 of FIG. 4. The input beam 601 is thus of nanosecond pulses at a wavelength of 1064 nm, a pulse rate around a kilohertz, and pulse energy of about 2 mJ. The overall conversion efficiency of the wavelength converter 600 can be approximately 10% and thus the output beam 605 will have pulse energy about 0.2 mJ at a wavelength 213 nm.

If the amplified pulse wavelength is around 800 nm, then a wavelength converter for $4^{th}$ harmonics generation is required. One prior art converter is to produce $2^{nd}$ harmonics with a LBO and then converts the $2^{nd}$ harmonics to $4^{th}$ harmonics with a BBO.

Although the above description is based on preferred embodiments, various modifications can be made without departing from the scopes of the appended claims.

What is claimed is:

1. A solid-state deep UV laser source for customized ablation in photo-refractive surgery comprises:
   a diode pumped laser oscillator producing nanosecond pulses at a kilohertz pulsed rate, wherein said oscillator is operated at a wavelength around 800 or 1000 nm and generates a pulsed laser beam close to diffraction limit;
   a multiple pass, diode pumped laser amplifier amplifying the nanosecond laser pulses to a mJ level; and
   a wavelength converter converting the amplified pulses to a wavelength around 200 nm and generating deep UV laser pulses to 100-microWatt level.

2. A solid-state deep UV laser source as in claim 1 wherein said laser oscillator is a passively-Q-switched microchip laser.

3. A solid-state deep UV laser source as in claim 1 wherein said laser oscillator has pulse duration of about a nanosecond.

4. A solid-state deep UV laser source as in claim 1 wherein said laser oscillator uses a laser crystal including Ti:sapphire, Cr:LiSAF, Nd:YAG, Nd:YLF, Nd:YVO, and Yb:YAG.

5. A solid-state deep UV laser source as in claim 1 wherein said laser amplifier is configured with two concave mirrors and one flat mirror.

6. A solid-state deep UV laser source as in claim 1 wherein said laser amplifier is aligned to have non-collinear spot disposition on the cavity mirrors of the amplifier.

7. A solid-state deep UV laser source as in claim 1 wherein said laser amplifier uses a gain medium crystal including Ti:sapphire, Cr:LiSAF, Nd:YAG, Nd:YLF, Nd:YVO, and Yb:YAG.

8. A solid-state deep UV laser source as in claim 1 wherein said wavelength converter consists of two or three non-linear crystals.

9. A solid-state deep UV laser source as in claim 1 wherein said wavelength converter consists of non-linear crystal LBO, BBO, and/or CLBO.

10. A solid-state deep UV laser source comprises:
    a diode pumped microchip laser producing nanosecond pulses at a repetition rate in the range of 0.5–5 kilohertz, wherein said oscillator is operated at a wavelength around 800 or 1000 nm and generates a pulsed laser beam close to diffraction limit;
    a multiple pass, diode pumped laser amplifier amplifying the nanosecond laser pulses to a mJ level; and
    a wavelength converter converting the amplified pulses to a wavelength around 200 nm and generating deep UV laser pulses to 100-microWatt level.

11. A solid-state deep UV laser source as in claim 10 wherein said microchip laser is a passively-Q-switched laser.

12. A solid-state deep UV laser source as in claim 10 wherein said microchip laser has pulse duration of about a nanosecond.

13. A solid-state deep UV laser source as in claim 10 wherein said laser amplifier is configured with two concave mirrors and one flat mirror.

14. A solid-state deep UV laser source as in claim 10 wherein said laser amplifier is aligned to have non-collinear spot disposition on the cavity mirrors of the amplifier.

15. A solid-state deep UV laser source as in claim 10 wherein said wavelength converter consists of non-linear crystal LBO, BBO, and/or CLBO.

16. A method for producing a solid-state deep UV laser source comprises the steps of:
    providing a diode pumped microchip laser producing nanosecond pulses at a repetition rate in the range of 0.5–5 kilohertz, operating at a wavelength around 800 or 1000 nm, and generating a pulsed laser beam close to diffraction limit;
    providing a multiple-pass diode pumped laser amplifier amplifying the nanosecond laser pulses to a mJ level; and
    providing a wavelength converter converting the amplified pulses to a wavelength around 200 nm and generating deep UV laser pulses to 100-microWatt level.

17. A method as in claim 16 wherein said step of providing a diode pumped microchip laser includes providing a passively-Q-switched laser.

18. A method as in claim 16 wherein said step of providing a laser amplifier includes providing a laser amplifier configured with two concave mirrors and one flat mirror.

19. A method as in claim 16 wherein said step of providing a laser amplifier includes providing a laser amplifier aligned to have non-collinear spot disposition on the cavity mirrors of the amplifier.

20. A method as in claim 16 wherein said step of providing a wavelength converter includes providing a wavelength converter consisting of non-linear crystal LBO, BBO, and/or CLBO.

* * * * *